US012697157B2

(12) United States Patent
Manwill

(10) Patent No.: US 12,697,157 B2
(45) Date of Patent: Aug. 4, 2026

(54) RETAINING DRIVER SYSTEM

(71) Applicant: Nexus Spine, LLC, Draper, UT (US)

(72) Inventor: Daniel Manwill, Draper, UT (US)

(73) Assignee: Nexus Spine, LLC, Draper, UT (US)

( * ) Notice: Subject to any disclaimer, the term of this patent is extended or adjusted under 35 U.S.C. 154(b) by 576 days.

(21) Appl. No.: 18/102,078

(22) Filed: Jan. 26, 2023

(65) Prior Publication Data

US 2023/0346444 A1    Nov. 2, 2023

Related U.S. Application Data

(60) Provisional application No. 63/303,413, filed on Jan. 26, 2022.

(51) Int. Cl.
*A61B 17/88*        (2006.01)
*A61B 17/17*        (2006.01)
(Continued)

(52) U.S. Cl.
CPC ...... *A61B 17/8886* (2013.01); *A61B 17/1725* (2013.01); *A61B 17/1728* (2013.01);
(Continued)

(58) Field of Classification Search
CPC ............ A61B 17/8888; A61B 17/8886; A61B 17/8615; A61B 17/8875; A61B 17/888; A61B 17/8877; A61B 17/8894; A61B 17/17; A61B 17/1725; A61B 17/1728; A61B 17/58; A61B 17/7082; A61B 17/86; A61B 17/8605; A61B 17/861; B25B 15/005; B25B 15/00; B25B 15/001; B25B 15/004; B25B 15/02; B25B 15/04; B25B 13/105; B25B 13/00; B25B 13/46;

B25B 13/467; B25B 23/00; B25B 23/0014; B25B 23/0035; B25B 23/0042; B25B 23/005; B25B 23/0071; B25B 23/08; B25B 23/10; B25B 23/101; B25B 23/106; B25B 23/103; B25B 23/108; B25B 23/02; B25B 23/105
USPC ........ 606/104, 916; 81/52, 55, 57.16, 57.34, 81/57.4, 59.1, 436, 442, 443, 444, 446, 81/448, 449
See application file for complete search history.

(56) References Cited

U.S. PATENT DOCUMENTS 6,565,573 B1 *  5/2003  Ferrante ............... A61B 17/863
                                                        606/62
8,894,687 B2    11/2014  Hawkes et al.
(Continued)

FOREIGN PATENT DOCUMENTS

AU        2013334732 A1    8/2017
EP          2517660 A1    3/2018
(Continued)

OTHER PUBLICATIONS

International Preliminary Search Report on Patentability for related International PCT Application No. PCT/US23/30862.

*Primary Examiner* — Marcela I. Shirsat
(74) *Attorney, Agent, or Firm* — Bryant Keller; John Oldroyd; Kirton MConkie

(57) ABSTRACT

Systems and methods for providing and using improved retaining drivers and screws. An undercut feature of the bone screw allows a corresponding selectively protruding retaining feature of the driver engage the undercut feature to retain the bone screw on the driver until selectively released.

16 Claims, 13 Drawing Sheets

(51) Int. Cl.

| | |
|---|---|
| *A61B 17/58* | (2006.01) |
| *A61B 17/70* | (2006.01) |
| *A61B 17/86* | (2006.01) |
| *B25B 13/10* | (2006.01) |
| *B25B 13/46* | (2006.01) |
| *B25B 15/00* | (2006.01) |
| *B25B 15/02* | (2006.01) |
| *B25B 23/00* | (2006.01) |
| *B25B 23/08* | (2006.01) |
| *B25B 23/10* | (2006.01) |

(52) U.S. Cl.
CPC ........... *A61B 17/58* (2013.01); *A61B 17/7082* (2013.01); *A61B 17/8605* (2013.01); *A61B 17/861* (2013.01); *A61B 17/8615* (2013.01); *A61B 17/8875* (2013.01); *A61B 17/8877* (2013.01); *A61B 17/888* (2013.01); *A61B 17/8888* (2013.01); *A61B 17/8894* (2013.01); *B25B 13/105* (2013.01); *B25B 13/46* (2013.01); *B25B 13/467* (2013.01); *B25B 15/001* (2013.01); *B25B 15/004* (2013.01); *B25B 15/005* (2013.01); *B25B 15/02* (2013.01); *B25B 23/0014* (2013.01); *B25B 23/0035* (2013.01); *B25B 23/0042* (2013.01); *B25B 23/005* (2013.01); *B25B 23/0071* (2013.01); *B25B 23/08* (2013.01); *B25B 23/10* (2013.01); *B25B 23/101* (2013.01); *B25B 23/103* (2013.01)

(56) References Cited

U.S. PATENT DOCUMENTS

| | | | | |
|---|---|---|---|---|
| 9,232,965 | B2 | 1/2016 | Hawkes | |
| 9,867,640 | B2 | 1/2018 | Ensign et al. | |
| 10,368,915 | B2 | 8/2019 | Ensign et al. | |
| 12,364,511 | B2 | 7/2025 | Ensign et al. | |
| 12,446,928 | B2 | 10/2025 | Hawkes et al. | |
| 2004/0230100 | A1* | 11/2004 | Shluzas | A61B 17/7082 |
| | | | | 600/208 |
| 2016/0074074 | A1 | 3/2016 | Hawkes | |
| 2016/0120576 | A1 | 5/2016 | Hawkes | |
| 2017/0020571 | A1 | 1/2017 | Hawkes et al. | |
| 2018/0103966 | A1* | 4/2018 | Jones | A61B 17/1764 |
| 2022/0142684 | A1* | 5/2022 | Manson | A61B 17/7076 |
| 2024/0058044 | A1 | 2/2024 | Halverson et al. | |
| 2025/0082370 | A1 | 3/2025 | Hawkes et al. | |
| 2025/0248743 | A1 | 8/2025 | Hawkes | |

FOREIGN PATENT DOCUMENTS

| | | | |
|---|---|---|---|
| EP | 3416573 | A1 | 12/2018 |
| EP | 2911599 | A1 | 4/2020 |
| EP | 2120749 | B1 | 5/2020 |
| EP | 2408389 | B1 | 4/2021 |
| WO | 2009021115 | A2 | 2/2009 |
| WO | 2024044211 | A1 | 2/2024 |

* cited by examiner

60

RETAINING DRIVER SYSTEM

TECHNICAL FIELD

The present invention relates to drivers such as screw drivers, and more particularly to retaining drivers and driver systems for surgical fasteners such as bone screws.

BACKGROUND ART

In surgery, surgical fasteners such as bone screws must be maintained sterile and are typically actuated to effectuate fastening in a surgical wound. One problem with existing fastening actuators (e.g., drivers for surgical screws such as bone screws) occurs when a fastening actuator does not secure the fastener before the fastener is affixed in the patient. What may occur is that the fastener may inadvertently disengage from the actuator and fall either outside the surgical wound (such as to the floor or other non-sterile location), thus requiring replacement or sterilization of the fastener, or into the surgical wound, potentially being lost or requiring effort to retrieve. Additionally, if the fastener is not retained, misalignment or disengagement may occur, leading to damage of the actuator and/or fastener, and/or injury to the patient.

Accordingly, for these reasons, surgeons typically prefer drivers that can retain surgical screws such as bone screws. Unfortunately, existing screw retention systems and methods have various deficiencies. Some drivers have a tapered tip that frictionally engages the screw, but is subject to accidental knock-off. Bone wax has been used as an improvised screw holder, but there is no guarantee of full engagement and a potential for accidental knock-off remains. Threaded engagement mechanisms are slow to engage or disengage, and are easily damaged. Split tip drivers have a potential to require a high pull-out force, don't fully address the potential for knock-off, and have a potential for compromised torsional strength. External sleeves such as nitinol or rubber sleeves are bulky, impede visualization, don't fully address the potential for knock-off, and may require manual reset between screws.

Accordingly, for reasons such as these, while surgeons prefer retaining drivers, existing retaining drivers fail to address the needs of surgeons that the drivers are attempting to address.

BRIEF SUMMARY OF THE INVENTION

Implementation of the invention provides improved retaining drivers and accompanying fasteners that address the deficiencies of previous devices and systems. Implementation of the invention also provides methods for manufacturing improved retaining drivers and accompanying fasteners, as well as methods for utilizing improved retaining drivers and accompanying fasteners. Implementations of the invention are particularly envisioned for use in bone fixation procedures, whereby the drivers and fasteners are bone screw drivers and bone screws, respectively, and in particular, pedicle bone screws for spinal fusion procedures.

Certain implementations of the invention provide a bone screw having a driving orifice, similar in certain regards to driving orifices that are known in the art. In some implementations, the driving orifice is a hexalobe orifice. The driving orifice is provided with an undercut feature, such as on one or more inwardly protruding driving features of the driving orifice, such that the undercut feature causes the driving orifice to have an increased inner diameter distal to a proximal opening of the driving orifice, such that the driving orifice is larger distally than it is proximally. The undercut feature allows a retaining element of a driver to engage the bone screw to retain the bone screw on the driver. In some implementations, the undercut feature is circumferential so the bone screw can be retained in any available rotational orientation. In other implementations, the undercut feature is only provided at certain screw orientations.

Certain implementations of the invention provide a driver having an access window such that a retaining element is permitted to protrude into a space between driver driving features. In some implementations, the driving features are lobes of a hexalobe driver bit. In such implementations, the retaining element is capable of extending through the access window into a space between the lobes of the hexalobe driver bit. When the driver bit is inserted into the driving orifice of the bone screw, the retaining element is positioned in a withdrawn position, such that the retaining element does not prevent entry of the driver bit into the driving orifice of the bone screw. Once the driver bit is positioned within the driving orifice, the retaining element is extended into the undercut feature such that the bone screw is retained on the driver bit.

Certain implementations of the invention provide an actuating element that causes the retaining element to selectively extend through the access window to engage the undercut feature of the bone screw. In some implementations, the actuating element includes a linear cam. In some implementations, the retaining element is spherical. In some implementations, the actuating element further serves to tension the retaining element against the bone screw so as to reduce or eliminate slop or play between the bone screw and the driver. To release the screw, the actuating element is actuated, thereby causing or allowing the retaining element to move inward, disengaging the retaining element from the undercut feature of the bone screw, allowing the bone screw and driver to be separated with minimal to no resistance.

In certain implementations, the cam portion of the actuating element includes a plurality of angled profiles. A release portion includes a flat portion that extends generally parallel to a long axis of the actuating element. A primary ramp portion is adjacent to the release portion, and includes a high-slope ramp to quickly move the retaining element into the access window and the undercut element. A secondary ramp portion is adjacent to the primary ramp (on an opposite end from the release portion) and has a low-slope ramp to prevent or minimize back-driving and to tension the retaining element against the bone screw.

In some implementations, the actuating element is operated using a trigger disposed on a shaft of the driver proximate a handle thereof. In other embodiments, the actuating element is operated using a trigger disposed on a handle of the driver. In some implementations, the actuating element is disposed in a lumen or channel disposed in a shaft of the driver. In some embodiments, the driver has an articulating tip wherein an actuating force applied at the handle is transferred through a joint of the driver to the actuating element at the driver bit.

According to certain implementations of the invention, a retaining driver for bone screws includes a shaft including a proximal end and a distal end and an elongate channel extending within the shaft from distal end toward the proximal end. The retaining driver further includes a retaining tip on the distal end of the shaft. The retaining tip includes a geometric profile adapted to permit transference of rotational torque to a corresponding geometric profile of a bone screw, a window formed on a side of the retaining tip and forming a passage communicating with the elongate channel, and a retaining element disposed within the passage and sized to be able to protrude from the window but not pass entirely through the window. The retaining driver further includes an elongate actuator at least partially and movingly disposed within the elongate channel, the elongate actuator including a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel.

In some implementations, the geometric profile of the retaining tip includes a profile such as a hexalobe profile (e.g., Torx™), a hex profile (e.g., Allen), a triple-square profile (e.g., Robertson), a Torx-Plus™ profile, or ball-tip versions of any of these profiles. In some implementations, the retaining element includes a form such as a sphere, a cylinder with a rounded tip, a pin, a plunger, a rectangular prism with a rounded tip, or a key.

In some implementations, the distal shape of the elongate actuator includes a cam profile including a dwell at release position at a most distal portion, a primary ramp proximally adjacent the dwell at release position adapted to provide a first, greater (relative to distal motion of the elongate actuator) displacement of the retaining element, and a secondary ramp proximally adjacent the primary ramp adapted to provide a second, lesser (relative to distal motion of the elongate actuator) displacement of the retaining element to reduce backdriving and to tension the retaining element in the bone screw. In some implementations, distal-proximal movement of the elongate actuator within the elongate shaft is provided by movement such as sliding movement, rotary movement, or helical movement.

In some implementations, the retaining driver further includes a handle fixedly attached to or formed with the shaft to facilitate holding of the retaining driver by a surgeon and application of rotational torque thereto, and a trigger functionally secured to a proximal end of the elongate actuator, such that actuation of the trigger causes the elongate actuator to move so as to cause the retaining element to move axially outward or to be released to permit inward axial movement of the retaining element as desired.

In some implementations, the retaining driver further includes an interface affixed to the proximal end of the shaft to permit affixation of the interface to a handle to facilitate holding of the retaining driver by a surgeon and application of rotational torque thereto, and a trigger functionally secured to a proximal end of the elongate actuator and disposed on the shaft, such that actuation of the trigger causes the elongate actuator to move so as to cause the retaining element to move axially outward or to be released to permit inward axial movement of the retaining element as desired.

In some implementations, the retaining driver further includes an articulating joint on the shaft facilitating transference of rotational torque at the proximal end of the shaft to the distal end of the shaft even when the proximal end of the shaft and the distal end of the shaft are not coaxial. In some implementations, the trigger is disposed distally of the articulating joint. In some implementations, the trigger is disposed proximally of the articulating joint and the elongate actuator passes through the articulating joint in an articulating form such as an articulating actuator joint formed in the elongate actuator or a flexible portion of the elongate actuator such as a nitinol wire, a metal cable, an ultra-high molecular weight polyethylene rod, or a coil spring.

In some implementations, the retaining element is one of a plurality of retaining elements that selectively protrudes through a plurality of windows on the retaining tip to selectively retain the bone screw thereon.

According to further implementations of the invention, a retaining driver system includes a bone screw and a retaining driver. The bone screw includes a threaded shaft having a proximal end and a distal tip, a screw head extending proximally from the proximal end of the threaded shaft, and a drive feature extending distally into the screw head from a drive feature opening. The drive feature includes a geometric profile adapted to receive transference of rotational torque when driving the bone screw into bone or when removing the bone screw from bone and an undercut feature dispose within the drive feature distally from the drive feature opening, such that a diameter of the drive feature distal the drive feature opening is greater than a diameter of the drive feature opening directly proximate the undercut feature. The retaining driver includes a shaft including a proximal end and a distal end, an elongate channel extending within the shaft from distal end toward the proximal end, and a retaining tip on the distal end of the shaft. The retaining tip includes a geometric profile adapted to permit transference of rotational torque to the geometric profile of the bone screw, a window formed on a side of the retaining tip so as to be aligned with the undercut feature of the bone screw when the retaining tip is fully inserted into the drive feature of the bone screw, the window forming a passage communicating with the elongate channel, and a retaining element disposed within the passage and sized to be able to protrude from the window but not pass entirely through the window. The retaining driver also includes an elongate actuator at least partially and movingly disposed within the elongate channel, the elongate actuator including a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel.

In some implementations, the geometric profile of the retaining tip includes a profile such as a hexalobe profile (e.g., Torx™), a hex profile (e.g., Allen), a triple-square profile (e.g., Robertson), a Torx-Plus™ profile, or ball-tip versions of any of these profiles. In some implementations, the retaining element includes a form such as a sphere, a cylinder with a rounded tip, a pin, a plunger, a rectangular prism with a rounded tip, or a key.

In some implementations, the distal shape of the elongate actuator includes a cam profile including a dwell at release position at a most distal portion, a primary ramp proximally adjacent the dwell at release position adapted to provide a first, greater (relative to distal motion of the elongate actuator) displacement of the retaining element, and a secondary ramp proximally adjacent the primary ramp adapted to provide a second, lesser (relative to distal motion of the elongate actuator) displacement of the retaining element to reduce backdriving and to tension the retaining element in the bone screw. In some implementations, distal-proximal movement of the elongate actuator within the elongate shaft is provided by movement such as sliding movement, rotary movement, or helical movement.

In some implementations, the retaining driver further includes a handle fixedly attached to or formed with the shaft to facilitate holding of the retaining driver by a surgeon and application of rotational torque thereto, and a trigger functionally secured to a proximal end of the elongate actuator, such that actuation of the trigger causes the elongate actuator to move so as to cause the retaining element to move axially outward or to be released to permit inward axial movement of the retaining element as desired.

In some implementations, the retaining driver further includes an interface affixed to the proximal end of the shaft to permit affixation of the interface to a handle to facilitate holding of the retaining driver by a surgeon and application of rotational torque thereto, and a trigger functionally secured to a proximal end of the elongate actuator and disposed on the shaft, such that actuation of the trigger causes the elongate actuator to move so as to cause the retaining element to move axially outward or to be released to permit inward axial movement of the retaining element as desired.

In some implementations, the retaining driver further includes an articulating joint on the shaft facilitating transference of rotational torque at the proximal end of the shaft to the distal end of the shaft even when the proximal end of the shaft and the distal end of the shaft are not coaxial. In some implementations, the trigger is disposed distally of the articulating joint. In some implementations, the trigger is disposed proximally of the articulating joint and the elongate actuator passes through the articulating joint in an articulating form such as an articulating actuator joint formed in the elongate actuator or a flexible portion of the elongate actuator such as a nitinol wire, a metal cable, an ultra-high molecular weight polyethylene rod, or a coil spring.

In some implementations, the retaining element is one of a plurality of retaining elements that selectively protrudes through a plurality of windows on the retaining tip to selectively retain the bone screw thereon.

According to further implementations of the invention, a retaining driver system includes a bone screw and a retaining driver. The bone screw includes a threaded shaft having a proximal end and a distal tip, a screw head extending proximally from the proximal end of the threaded shaft, and a hexalobe drive feature extending distally into the screw head from a drive feature opening. The hexalobe drive feature includes a hexalobe profile adapted to receive transference of rotational torque when driving the bone screw into bone or when removing the bone screw from bone and an undercut feature dispose within the hexalobe drive feature distally from the drive feature opening, such that a diameter of the drive feature distal the drive feature opening is greater than a diameter of the drive feature opening directly proximate the undercut feature. The retaining driver includes a shaft including a proximal end and a distal end, an elongate channel extending within the shaft from distal end toward the proximal end, and a retaining tip on the distal end of the shaft. The retaining tip includes a hexalobe profile adapted to permit transference of rotational torque to the hexalobe drive feature of the bone screw, a window formed on a side of the retaining tip so as to be aligned with the undercut feature of the bone screw when the retaining tip is fully inserted into the drive feature of the bone screw, the window forming a passage communicating with the elongate channel, and a retaining element disposed within the passage and sized to be able to protrude from the window but not pass entirely through the window. The retaining driver further includes an elongate actuator at least partially and movingly disposed within the elongate channel, the elongate actuator including a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel.

In some implementations, the retaining element includes a form such as a sphere, a cylinder with a rounded tip, a pin, a plunger, a rectangular prism with a rounded tip, or a key.

In some implementations, the distal shape of the elongate actuator includes a cam profile including a dwell at release position at a most distal portion, a primary ramp proximally adjacent the dwell at release position adapted to provide a first, greater (relative to distal motion of the elongate actuator) displacement of the retaining element, and a secondary ramp proximally adjacent the primary ramp adapted to provide a second, lesser (relative to distal motion of the elongate actuator) displacement of the retaining element to reduce backdriving and to tension the retaining element in the bone screw. In some implementations, distal-proximal movement of the elongate actuator within the elongate shaft is provided by movement such as sliding movement, rotary movement, or helical movement.

In some implementations, the retaining driver further includes a handle fixedly attached to or formed with the shaft to facilitate holding of the retaining driver by a surgeon and application of rotational torque thereto, and a trigger functionally secured to a proximal end of the elongate actuator, such that actuation of the trigger causes the elongate actuator to move so as to cause the retaining element to move axially outward or to be released to permit inward axial movement of the retaining element as desired.

In some implementations, the retaining driver further includes an interface affixed to the proximal end of the shaft to permit affixation of the interface to a handle to facilitate holding of the retaining driver by a surgeon and application of rotational torque thereto, and a trigger functionally secured to a proximal end of the elongate actuator and disposed on the shaft, such that actuation of the trigger causes the elongate actuator to move so as to cause the retaining element to move axially outward or to be released to permit inward axial movement of the retaining element as desired.

In some implementations, the retaining driver further includes an articulating joint on the shaft facilitating transference of rotational torque at the proximal end of the shaft to the distal end of the shaft even when the proximal end of the shaft and the distal end of the shaft are not coaxial. In some implementations, the trigger is disposed distally of the articulating joint. In some implementations, the trigger is disposed proximally of the articulating joint and the elongate actuator passes through the articulating joint in an articulating form such as an articulating actuator joint formed in the elongate actuator or a flexible portion of the elongate actuator such as a nitinol wire, a metal cable, an ultra-high molecular weight polyethylene rod, or a coil spring.

In some implementations, the retaining element is one of a plurality of retaining elements that selectively protrudes through a plurality of windows on the retaining tip to selectively retain the bone screw thereon.

Implementations of the invention provide benefits over prior retaining drivers. In particular, the retaining mechanism is fully contained within the screw head during use, thereby eliminating tissue snagging and preserving visualization for the surgeon. The system provides positive retention, ensuring full engagement of the driving feature and no possibility of screw knock-off. The system also provides for kinematic engagement and release, such that there is no need to apply significant force to the screw to obtain engagement on or separation from the driver. The system continues to perform well at securing the bone screw even as the driver wears. The system provides for quick retention and release of the bone screw, using a trigger or button instead of a threaded knob or sliding sleeve, and there is no need to manually reset the system between screws. The system also permits actuation through a universal joint or other articulating mechanism.

BRIEF DESCRIPTION OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying annotated drawings in which:

DETAILED DESCRIPTION OF THE INVENTION

Figure 1:
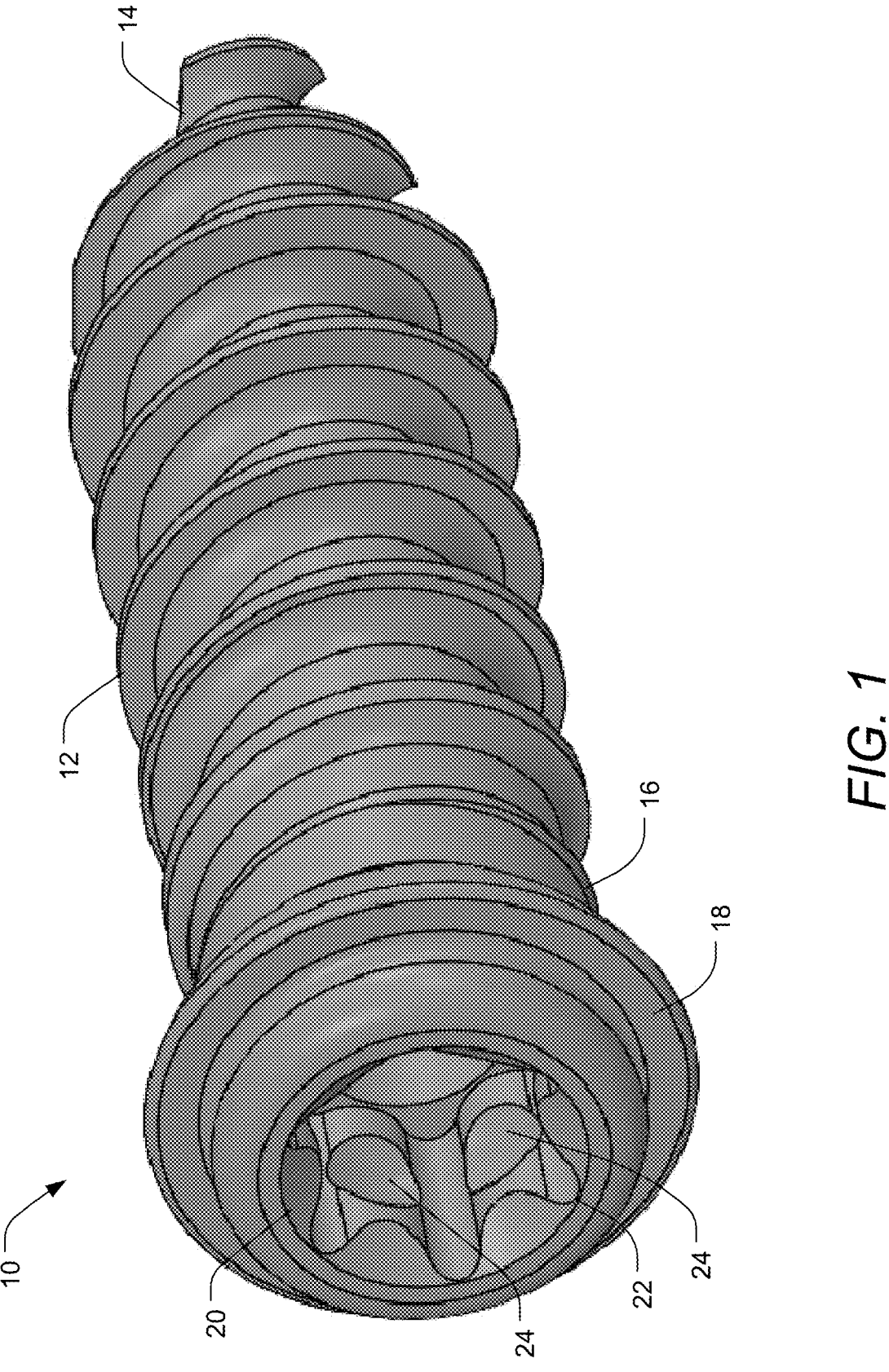
FIG. 1 shows a perspective view of a bone screw.

A description of embodiments of the present invention is given with reference to the Appendix. It is expected that the present invention may take many other forms and shapes, hence the following disclosure is intended to be illustrative and not limiting, and the scope of the invention should be determined by reference to the appended claims.

Embodiments of the invention provide improved retaining drivers and accompanying fasteners that address the deficiencies of previous devices and systems. Embodiments of the invention also provide methods for manufacturing improved retaining drivers and accompanying fasteners, as well as methods for utilizing improved retaining drivers and accompanying fasteners. Embodiments of the invention are particularly envisioned for use in bone fixation procedures, whereby the drivers and fasteners are bone screw drivers and bone screws, respectively, and, in particular, pedicle bone screws for spinal fusion procedures.

Certain embodiments of the invention provide a bone screw having a driving orifice, similar in certain regards to driving orifices that are known in the art. In some embodiments, the driving orifice is a hexalobe orifice. The driving orifice is provided with an undercut feature, such as on one or more inwardly protruding driving features of the driving orifice, such that the undercut feature causes the driving orifice to have an increased inner diameter distal to a proximal opening of the driving orifice, such that the driving orifice is larger distally than it is proximally. The undercut feature allows a retaining element of a driver to engage the bone screw to retain the bone screw on the driver. In some embodiments, the undercut feature is circumferential so the bone screw can be retained in any available rotational orientation. In other embodiments, the undercut feature is only provided at certain screw orientations.

Certain embodiments of the invention provide a driver having an access window such that a retaining element is permitted to protrude into a space between driver driving features. In some embodiments, the driving features are lobes of a hexalobe driver bit. In such embodiments, the retaining element is capable of extending through the access window into a space between the lobes of the hexalobe driver bit. When the driver bit is inserted into the driving orifice of the bone screw, the retaining element is positioned in a withdrawn position, such that the retaining element does not prevent entry of the driver bit into the driving orifice of the bone screw. Once the driver bit is positioned within the driving orifice, the retaining element is extended into the undercut feature such that the bone screw is retained on the driver bit.

Certain embodiments of the invention provide an actuating element that causes the retaining element to selectively extend through the access window to engage the undercut feature of the bone screw. In some embodiments, the actuating element includes a linear cam. In some embodiments, the retaining element is spherical. In some embodiments, the actuating element further serves to tension the retaining element against the bone screw so as to reduce or eliminate slop or play between the bone screw and the driver. To release the screw, the actuating element is actuated, thereby causing or allowing the retaining element to move inward, disengaging the retaining element from the undercut feature of the bone screw, allowing the bone screw and driver to be separated with minimal to no resistance.

In certain embodiments, the cam portion of the actuating element includes a plurality of angled profiles. A release portion includes a flat portion that extends generally parallel to a long axis of the actuating element. A primary ramp portion is adjacent to the release portion, and includes a high-slope ramp to quickly move the retaining element into the access window and the undercut element. A secondary ramp portion is adjacent to the primary ramp (on an opposite end from the release portion) and has a low-slope ramp to prevent or minimize back-driving and to tension the retaining element against the bone screw.

In some embodiments, the actuating element is operated using a trigger disposed on a shaft of the driver proximate a handle thereof. In other embodiments, the actuating element is operated using a trigger disposed on a handle of the driver. In some embodiments, the actuating element is disposed in a lumen or channel disposed in a shaft of the driver. In some embodiments, the driver has an articulating tip wherein an actuating force applied at the handle is transferred through a joint of the driver to the actuating element at the driver bit.

According to certain embodiments of the invention, a retaining driver for bone screws includes a shaft including a proximal end and a distal end and an elongate channel extending within the shaft from distal end toward the proximal end. The retaining driver further includes a retaining tip on the distal end of the shaft. The retaining tip includes a geometric profile adapted to permit transference of rotational torque to a corresponding geometric profile of a bone screw, a window formed on a side of the retaining tip and forming a passage communicating with the elongate channel, and a retaining element disposed within the passage and sized to be able to protrude from the window but not pass entirely through the window. The retaining driver further includes an elongate actuator at least partially and movingly disposed within the elongate channel, the elongate actuator including a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel.

In some embodiments, the geometric profile of the retaining tip includes a profile such as a hexalobe profile (e.g., Torx™), a hex profile (e.g., Allen), a triple-square profile (e.g., Robertson), a Torx-Plus™ profile, or ball-tip versions of any of these profiles. In some embodiments, the retaining element includes a form such as a sphere, a cylinder with a rounded tip, a pin, a plunger, a rectangular prism with a rounded tip, or a key.

In some embodiments, the distal shape of the elongate actuator includes a cam profile including a dwell at release position at a most distal portion, a primary ramp proximally adjacent the dwell at release position adapted to provide a first, greater (relative to distal motion of the elongate actuator) displacement of the retaining element, and a secondary ramp proximally adjacent the primary ramp adapted to provide a second, lesser (relative to distal motion of the elongate actuator) displacement of the retaining element to reduce backdriving and to tension the retaining element in the bone screw. In some embodiments, distal-proximal movement of the elongate actuator within the elongate shaft is provided by movement such as sliding movement, rotary movement, or helical movement.

In some embodiments, the retaining driver further includes a handle fixedly attached to or formed with the shaft to facilitate holding of the retaining driver by a surgeon and application of rotational torque thereto, and a trigger functionally secured to a proximal end of the elongate actuator, such that actuation of the trigger causes the elongate actuator to move so as to cause the retaining element to move axially outward or to be released to permit inward axial movement of the retaining element as desired.

In some embodiments, the retaining driver further includes an interface affixed to the proximal end of the shaft to permit affixation of the interface to a handle to facilitate holding of the retaining driver by a surgeon and application of rotational torque thereto, and a trigger functionally secured to a proximal end of the elongate actuator and disposed on the shaft, such that actuation of the trigger causes the elongate actuator to move so as to cause the retaining element to move axially outward or to be released to permit inward axial movement of the retaining element as desired.

In some embodiments, the retaining driver further includes an articulating joint on the shaft facilitating transference of rotational torque at the proximal end of the shaft to the distal end of the shaft even when the proximal end of the shaft and the distal end of the shaft are not coaxial. In some embodiments, the trigger is disposed distally of the articulating joint. In some embodiments, the trigger is disposed proximally of the articulating joint and the elongate actuator passes through the articulating joint in an articulating form such as an articulating actuator joint formed in the elongate actuator or a flexible portion of the elongate actuator such as a nitinol wire, a metal cable, an ultra-high molecular weight polyethylene rod, or a coil spring.

In some embodiments, the retaining element is one of a plurality of retaining elements that selectively protrudes through a plurality of windows on the retaining tip to selectively retain the bone screw thereon.

According to further embodiments of the invention, a retaining driver system includes a bone screw and a retaining driver. The bone screw includes a threaded shaft having a proximal end and a distal tip, a screw head extending proximally from the proximal end of the threaded shaft, and a drive feature extending distally into the screw head from a drive feature opening. The drive feature includes a geometric profile adapted to receive transference of rotational torque when driving the bone screw into bone or when removing the bone screw from bone and an undercut feature dispose within the drive feature distally from the drive feature opening, such that a diameter of the drive feature distal the drive feature opening is greater than a diameter of the drive feature opening directly proximate the undercut feature. The retaining driver includes a shaft including a proximal end and a distal end, an elongate channel extending within the shaft from distal end toward the proximal end, and a retaining tip on the distal end of the shaft. The retaining tip includes a geometric profile adapted to permit transference of rotational torque to the geometric profile of the bone screw, a window formed on a side of the retaining tip so as to be aligned with the undercut feature of the bone screw when the retaining tip is fully inserted into the drive feature of the bone screw, the window forming a passage communicating with the elongate channel, and a retaining element disposed within the passage and sized to be able to protrude from the window but not pass entirely through the window. The retaining driver also includes an elongate actuator at least partially and movingly disposed within the elongate channel, the elongate actuator including a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel.

In some embodiments, the geometric profile of the retaining tip includes a profile such as a hexalobe profile (e.g., Torx™), a hex profile (e.g., Allen), a triple-square profile (e.g., Robertson), a Torx-Plus™ profile, or ball-tip versions of any of these profiles. In some embodiments, the retaining element includes a form such as a sphere, a cylinder with a rounded tip, a pin, a plunger, a rectangular prism with a rounded tip, or a key.

In some embodiments, the distal shape of the elongate actuator includes a cam profile including a dwell at release position at a most distal portion, a primary ramp proximally adjacent the dwell at release position adapted to provide a first, greater (relative to distal motion of the elongate actuator) displacement of the retaining element, and a secondary ramp proximally adjacent the primary ramp adapted to provide a second, lesser (relative to distal motion of the elongate actuator) displacement of the retaining element to reduce backdriving and to tension the retaining element in the bone screw. In some embodiments, distal-proximal movement of the elongate actuator within the elongate shaft is provided by movement such as sliding movement, rotary movement, or helical movement.

In some embodiments, the retaining driver further includes a handle fixedly attached to or formed with the shaft to facilitate holding of the retaining driver by a surgeon and application of rotational torque thereto, and a trigger functionally secured to a proximal end of the elongate actuator, such that actuation of the trigger causes the elongate actuator to move so as to cause the retaining element to move axially outward or to be released to permit inward axial movement of the retaining element as desired.

In some embodiments, the retaining driver further includes an interface affixed to the proximal end of the shaft to permit affixation of the interface to a handle to facilitate holding of the retaining driver by a surgeon and application of rotational torque thereto, and a trigger functionally secured to a proximal end of the elongate actuator and disposed on the shaft, such that actuation of the trigger causes the elongate actuator to move so as to cause the retaining element to move axially outward or to be released to permit inward axial movement of the retaining element as desired.

In some embodiments, the retaining driver further includes an articulating joint on the shaft facilitating transference of rotational torque at the proximal end of the shaft to the distal end of the shaft even when the proximal end of the shaft and the distal end of the shaft are not coaxial. In some embodiments, the trigger is disposed distally of the articulating joint. In some embodiments, the trigger is disposed proximally of the articulating joint and the elongate actuator passes through the articulating joint in an articulating form such as an articulating actuator joint formed in the elongate actuator or a flexible portion of the elongate actuator such as a nitinol wire, a metal cable, an ultra-high molecular weight polyethylene rod, or a coil spring.

In some embodiments, the retaining element is one of a plurality of retaining elements that selectively protrudes through a plurality of windows on the retaining tip to selectively retain the bone screw thereon.

According to further embodiments of the invention, a retaining driver system includes a bone screw and a retaining driver. The bone screw includes a threaded shaft having a proximal end and a distal tip, a screw head extending proximally from the proximal end of the threaded shaft, and a hexalobe drive feature extending distally into the screw head from a drive feature opening. The hexalobe drive feature includes a hexalobe profile adapted to receive transference of rotational torque when driving the bone screw into bone or when removing the bone screw from bone and an undercut feature dispose within the hexalobe drive feature distally from the drive feature opening, such that a diameter of the drive feature distal the drive feature opening is greater than a diameter of the drive feature opening directly proximate the undercut feature. The retaining driver includes a shaft including a proximal end and a distal end, an elongate channel extending within the shaft from distal end toward the proximal end, and a retaining tip on the distal end of the shaft. The retaining tip includes a hexalobe profile adapted to permit transference of rotational torque to the hexalobe drive feature of the bone screw, a window formed on a side of the retaining tip so as to be aligned with the undercut feature of the bone screw when the retaining tip is fully inserted into the drive feature of the bone screw, the window forming a passage communicating with the elongate channel, and a retaining element disposed within the passage and sized to be able to protrude from the window but not pass entirely through the window. The retaining driver further includes an elongate actuator at least partially and movingly disposed within the elongate channel, the elongate actuator including a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel.

In some embodiments, the retaining element includes a form such as a sphere, a cylinder with a rounded tip, a pin, a plunger, a rectangular prism with a rounded tip, or a key.

In some embodiments, the distal shape of the elongate actuator includes a cam profile including a dwell at release position at a most distal portion, a primary ramp proximally adjacent the dwell at release position adapted to provide a first, greater (relative to distal motion of the elongate actuator) displacement of the retaining element, and a secondary ramp proximally adjacent the primary ramp adapted to provide a second, lesser (relative to distal motion of the elongate actuator) displacement of the retaining element to reduce backdriving and to tension the retaining element in the bone screw. In some embodiments, distal-proximal movement of the elongate actuator within the elongate shaft is provided by movement such as sliding movement, rotary movement, or helical movement.

In some embodiments, the retaining driver further includes a handle fixedly attached to or formed with the shaft to facilitate holding of the retaining driver by a surgeon and application of rotational torque thereto, and a trigger functionally secured to a proximal end of the elongate actuator, such that actuation of the trigger causes the elongate actuator to move so as to cause the retaining element to move axially outward or to be released to permit inward axial movement of the retaining element as desired.

In some embodiments, the retaining driver further includes an interface affixed to the proximal end of the shaft to permit affixation of the interface to a handle to facilitate holding of the retaining driver by a surgeon and application of rotational torque thereto, and a trigger functionally secured to a proximal end of the elongate actuator and disposed on the shaft, such that actuation of the trigger causes the elongate actuator to move so as to cause the retaining element to move axially outward or to be released to permit inward axial movement of the retaining element as desired.

In some embodiments, the retaining driver further includes an articulating joint on the shaft facilitating transference of rotational torque at the proximal end of the shaft to the distal end of the shaft even when the proximal end of the shaft and the distal end of the shaft are not coaxial. In some embodiments, the trigger is disposed distally of the articulating joint. In some embodiments, the trigger is disposed proximally of the articulating joint and the elongate actuator passes through the articulating joint in an articulating form such as an articulating actuator joint formed in the elongate actuator or a flexible portion of the elongate actuator such as a nitinol wire, a metal cable, an ultra-high molecular weight polyethylene rod, or a coil spring.

In some embodiments, the retaining element is one of a plurality of retaining elements that selectively protrudes through a plurality of windows on the retaining tip to selectively retain the bone screw thereon.

Embodiments of the invention provide benefits over prior retaining drivers. In particular, the retaining mechanism is fully contained within the screw head during use, thereby eliminating tissue snagging and preserving visualization for the surgeon. The system provides positive retention, ensuring full engagement of the driving feature and no possibility of screw knock-off. The system also provides for kinematic engagement and release, such that there is no need to apply significant force to the screw to obtain engagement on or separation from the driver. The system continues to perform well at securing the bone screw even as the driver wears. The system provides for quick retention and release of the bone screw, using a trigger or button instead of a threaded knob or sliding sleeve, and there is no need to manually reset the system between screws. The system also permits actuation through a universal joint or other articulating mechanism.

FIG. 1 illustrates one illustrative embodiment of a bone screw 10 in accordance with embodiments of the invention. The bone screw 10 includes a threaded shaft 12 adapted to be screwed into bone, such as into a pedicle during a spinal fusion procedure. The threaded shaft 12 has a distal tip 14 and a proximal end 16. A screw head 18 is located at the proximal end 16 of the threaded shaft 12 and permits transference of rotational torque applied at the screw head 18 to be transferred to the threaded shaft 12 so the bone screw 10 can be selectively driven into or removed from bone, such as during a surgical procedure.

The screw head 18 includes a driving feature 20 or driving orifice formed on a proximal end of the screw head 18 so as to be generally axially aligned with the threaded shaft 12, as is known in the art. The driving feature 20 has a geometric profile that permits transference of rotational force from a driver to the bone screw 10. In the illustrated embodiment, the geometric profile of the driving feature 20 is a hexalobe profile, such as a Torx™-type profile, but can be of a variety of other profiles, such as triangular, square, hex (Allen), triple-square (Robertson), Torx™-Plus, and the like. Accordingly, the geometric profile illustrated in FIG. 1 is not intended to be limiting.

The geometric profile of the driving feature 20 extends from a drive feature opening 22 distally a distance to permit secure engagement between a driver and the bone screw 10, as is known in the art. In contrast to existing bone screws, however, the geometric profile of the driving feature 20 includes one or more undercut features 24 that extend radially into the material of the screw head 18 such that the diameter of the driving feature 20 at the undercut feature 24 or undercut features 24 is greater than the diameter of the driving feature 20 at the drive feature opening 22. In the example illustrated in FIG. 1, the undercut features 24 are formed on protrusions of the geometric profile of the driving feature 20. The undercut features 24 of some embodiments is formed as a turned element during blanking of the bone screw 10 before the geometric profile (e.g., hexalobe features) are cut in the screw head 18.

Figure 2:
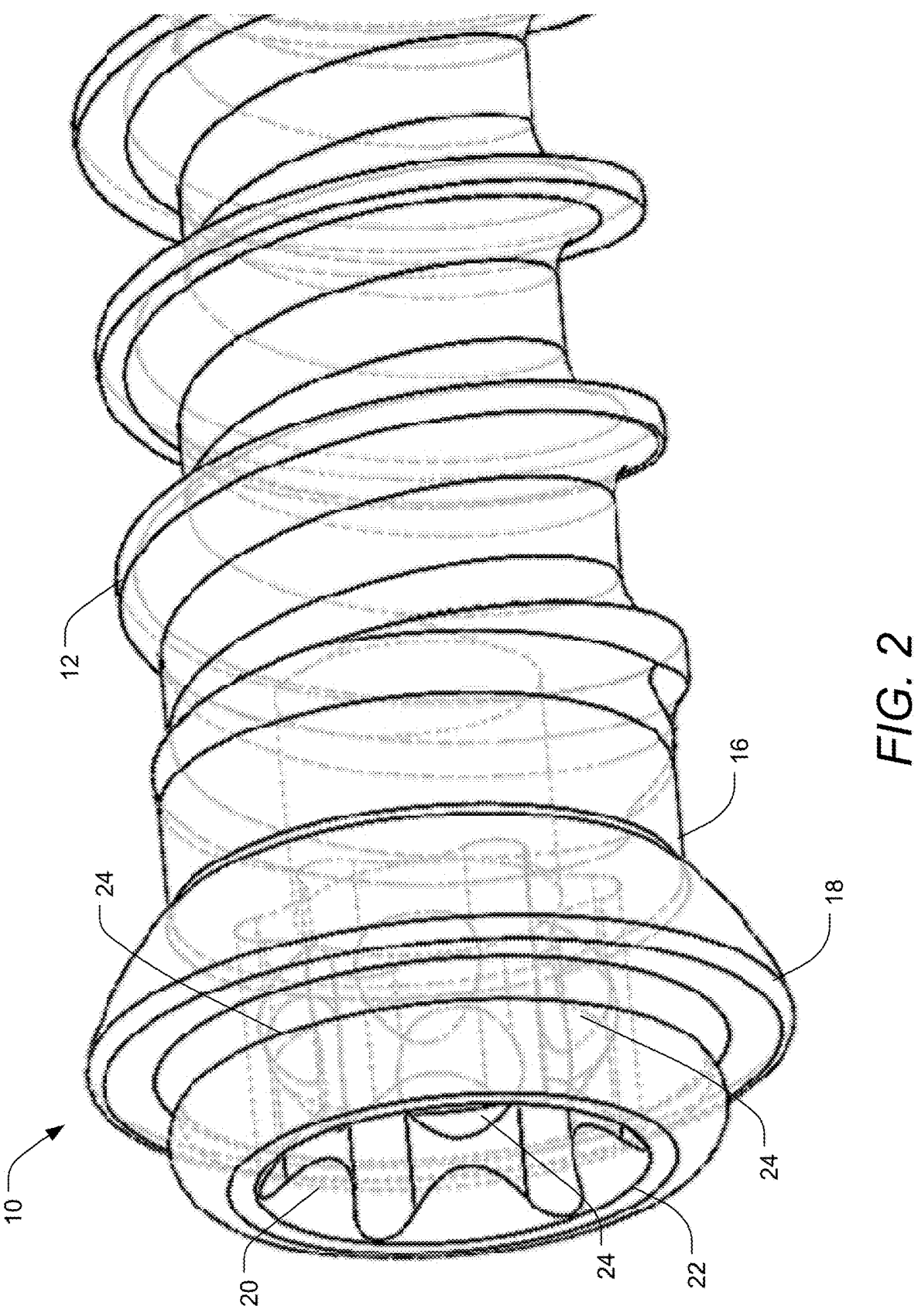
FIG. 2 shows a plan view of a portion of a bone screw.
Figure 3:
FIG. 3 shows a plan view of a head portion of a bone screw.

FIGS. 2 and 3 provide plan/transparent views of the embodiment of the bone screw 10 illustrated in FIG. 1 to further show the elements thereof discussed above. The bone screw 10 is adapted to be secured and retained on a retaining driver, where the retaining driver engages one or more of the undercut feature 24 or undercut features 24 to retain the bone screw 10 on the retaining driver. Accordingly, the retaining driver includes a retaining tip 30, such as is illustrated in one embodiment in FIG. 4. The retaining tip 30 is disposed at a distal end of the retaining driver, such as a distal end of an elongate shaft 32 that permits the retaining tip 30 to be disposed in a wound, including through a laparoscopic access point. The retaining tip 30 has a geometric profile 34, including one or a plurality of driving elements or fins that engage with corresponding features in the driving feature of the bone screw 10 to permit transference of rotational torque from the retaining tip 30 to the bone screw 10.

Figure 4:
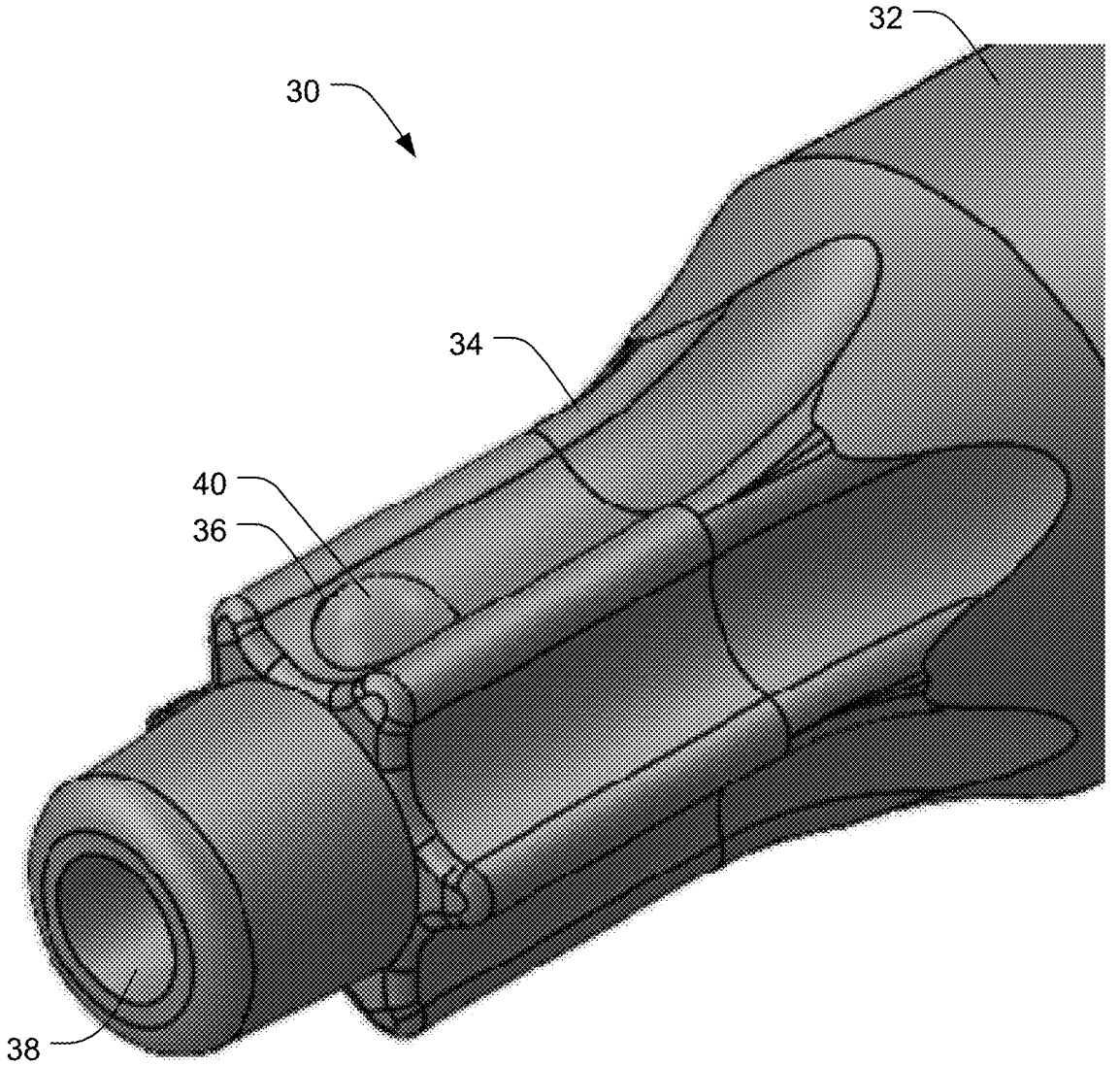
FIG. 4 shows a perspective view of a retaining tip of a retaining driver.

The retaining tip 30 further includes a window 36 formed on a surface thereof, such as in a hollow between protruding fins of the geometric profile 34. While the retaining tip 30 illustrated in FIG. 4 shows a single window 36, alternate embodiments of the retaining tip 30 include a plurality of radially arranged windows 36 disposed on the retaining tip 30. The window 36 connects to a passage that extends into the retaining tip to an elongate channel 38 that extends axially through the retaining tip 30 and into the elongate shaft 32. The passage houses a retaining element 40 that is sized so as to be able to protrude through the window 36 but to not pass entirely through the window 36 (thus being retained against falling out of the retaining tip 30). In some embodiments, the retaining element 40 is formed as a sphere, while in other embodiments the retaining element 40 takes other shapes as discussed above.

Figure 5:
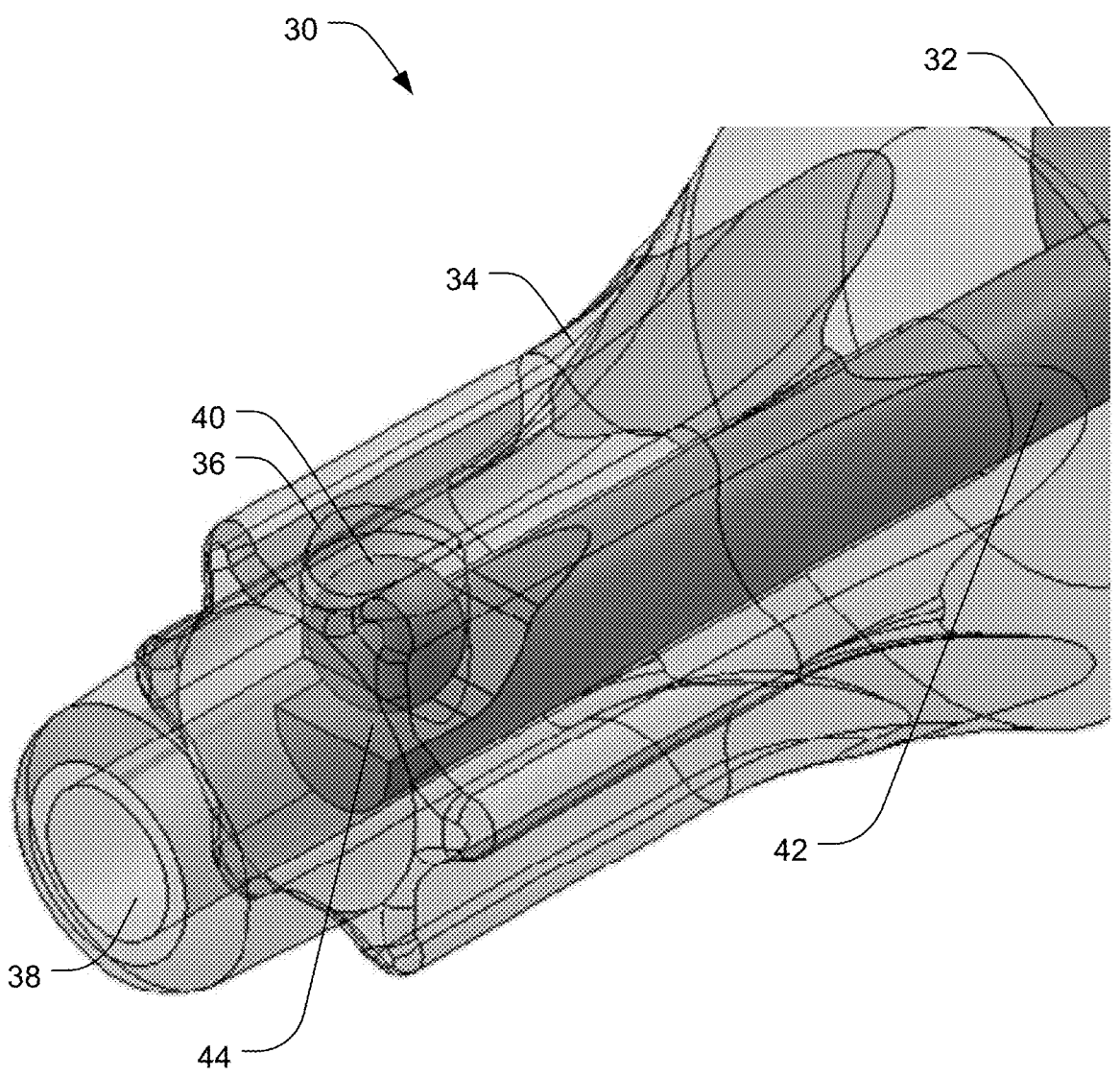
FIG. 5 shows a transparent view of a retaining tip of a retaining driver.

FIG. 5 shows a transparent view of the retaining tip 30 of FIG. 4, illustrating that an elongate actuator 42 is disposed in the elongate channel 38 so as to be able to actuate the retaining element 40. In the illustrated embodiment, the elongate actuator 42 actuates the retaining element 40 by way of sliding distal-proximal motion within the elongate channel 38, but in other embodiments, the elongate actuator 42 may act by other motions such as by rotational motion or helical motion. In the illustrated embodiment, the elongate actuator 42 includes a distal linear cam 44 having a profile that displaces the retaining element 40 radially outward as the elongate actuator 42 is advanced distally and that permits the retaining element 40 to move radially inward when the elongate actuator 42 is withdrawn proximally.

Figure 6:
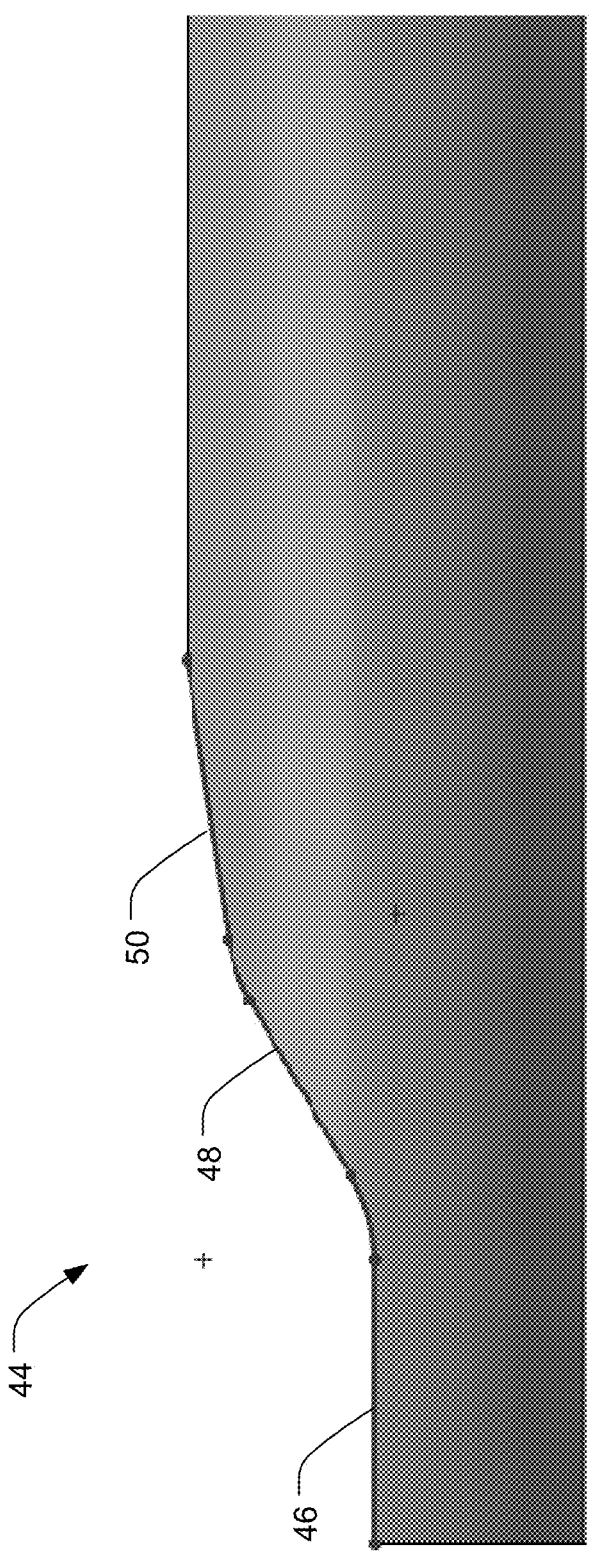
FIG. 6 shows a side profile view of a distal linear cam.

FIG. 6 shows a side profile of one embodiment of the distal linear cam 44. The distal linear cam 44 includes a dwell at release portion that is most distally located and that permits the retaining element 40 to be fully withdrawn. A primary ramp 48 is located proximally adjacent the dwell at release portion 46 and has a steeper profile so as to maximize radial movement of the retaining element 46 relative to the distal-proximal motion of the elongate actuator 42. A secondary ramp 50 is located proximally adjacent the primary ramp and has a gentler profile so as to prevent backdriving of the elongate actuator 42 and to tension the retaining element in the screw head 18 to reduce wobble of the retained bone screw 10.

Figure 7:
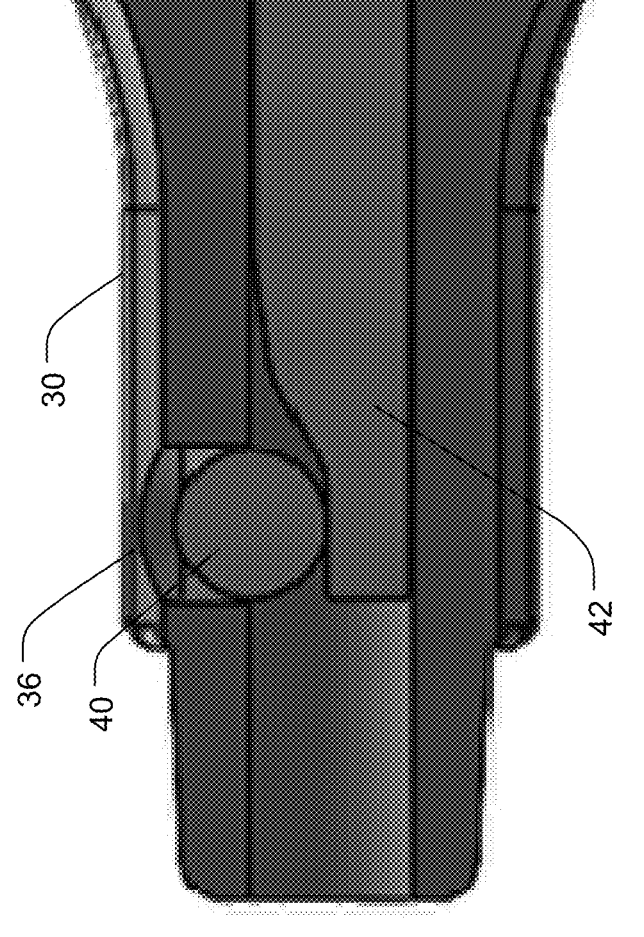
FIG. 7 shows a cutaway view of a retaining tip positioned for engagement with a bone screw.
Figure 7:
Figure 7:
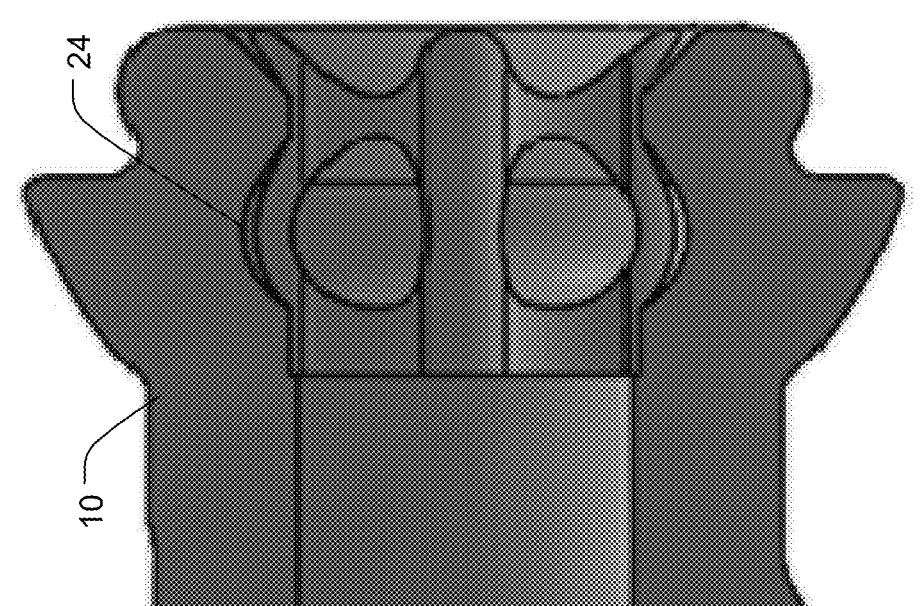
Figure 8:
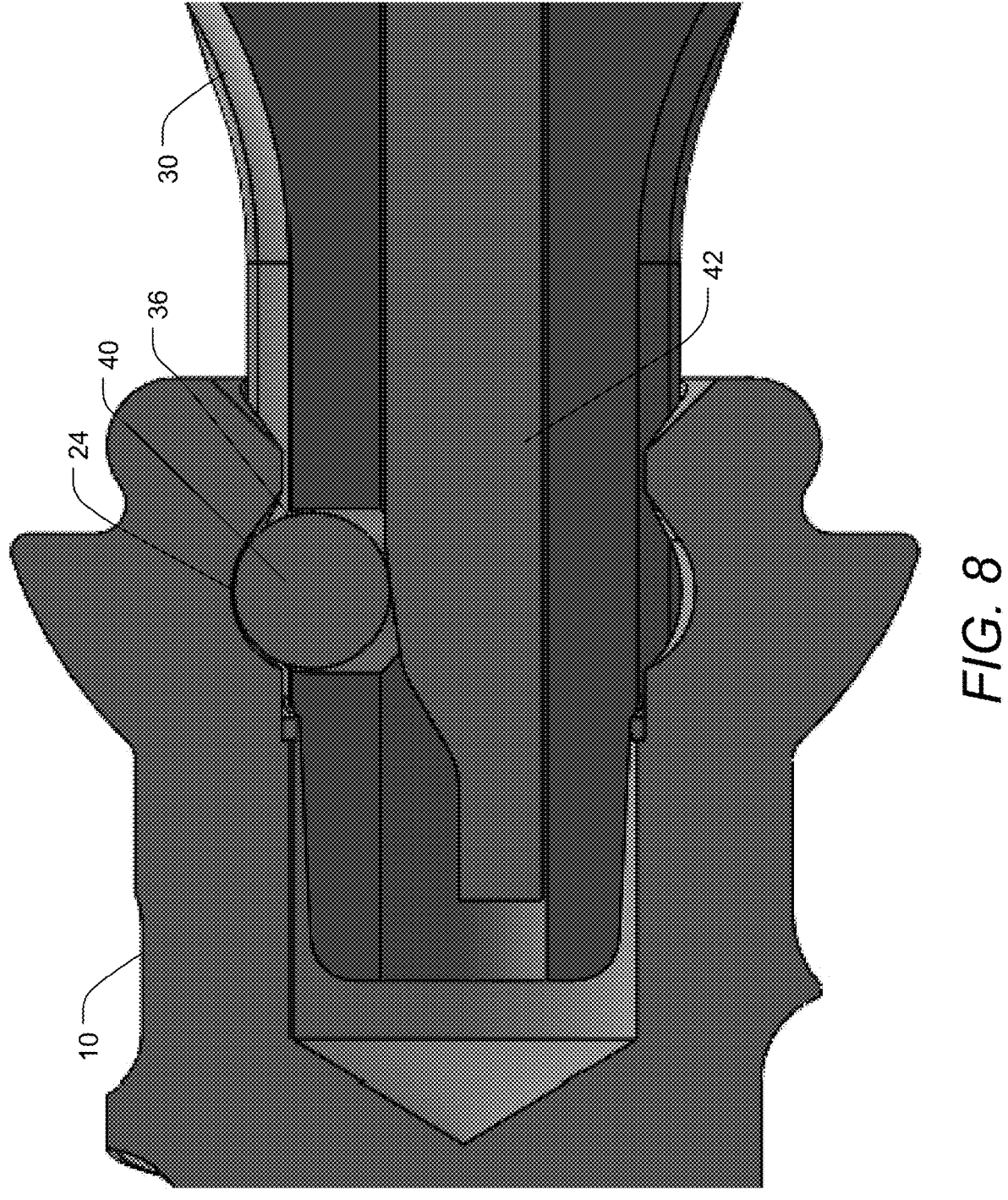
FIG. 8 shows a cutaway view of a retaining tip positioned in, engaging with, and securing a bone screw.
Figure 9:
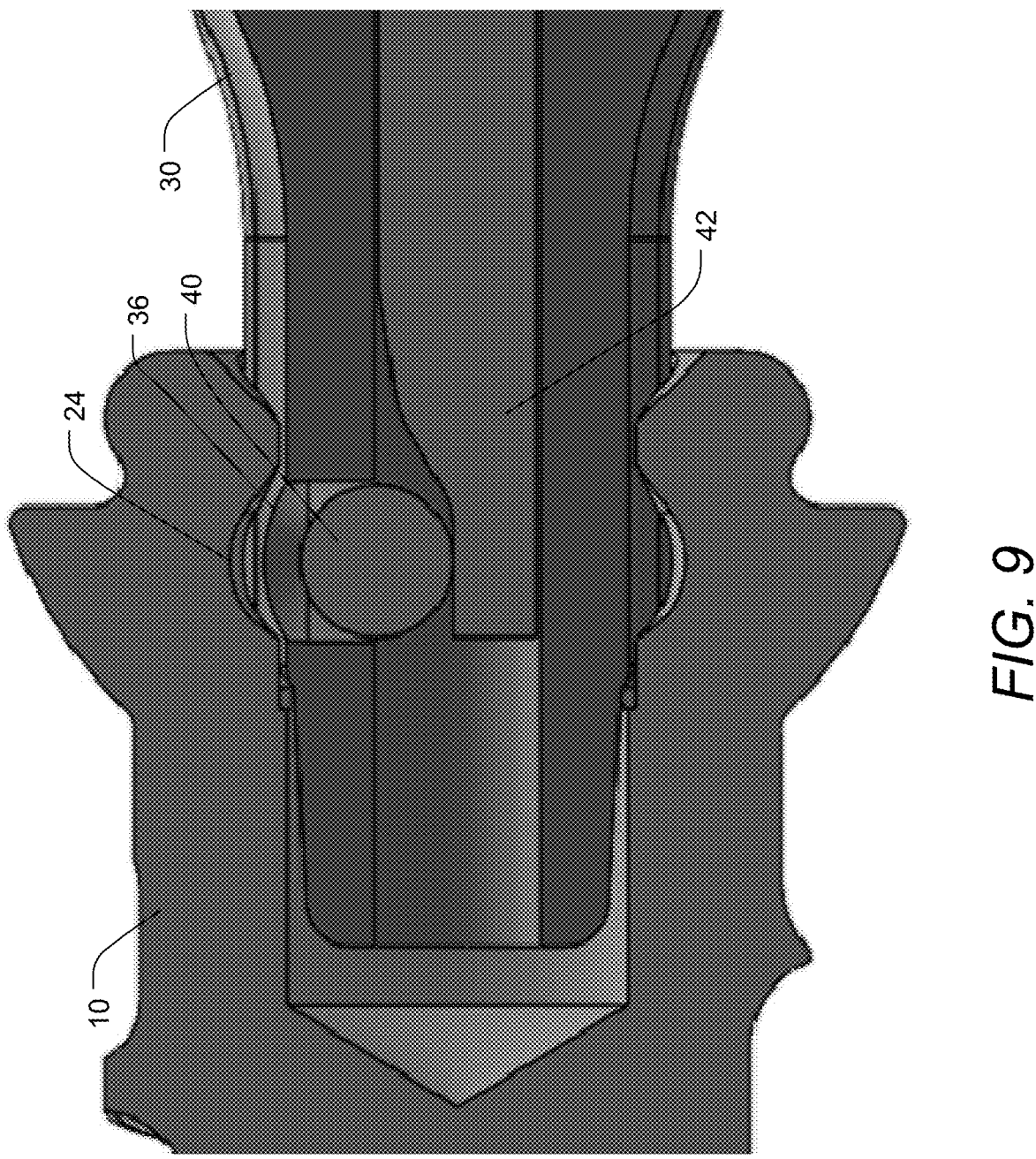
FIG. 9 shows a cutaway view of a retaining tip positioned in and engaging with, but not securing a bone screw.

FIGS. 7-9 illustrate cutaway views of the retaining tip 30 engaging a bone screw 10 so as to illustrate retaining of the bone screw 10 on the retaining tip 30 and release of the bone screw 10 from the retaining tip 30. As shown in FIG. 7, when the retaining tip 30 is to be inserted into the bone screw 10, the elongate actuator 42 is in its most-proximal position such that the retaining element 40 is withdrawn. Once the retaining tip 30 is fully inserted into the bone screw 10, as shown in FIG. 8, the elongate actuator 42 is advanced distally, forcing the retaining element 40 to be displaced radially outward such that the retaining element 40 fully engages the undercut feature 24, retaining the bone screw 10 against removal from the retaining tip 30. When the time comes to remove the retaining tip 30 from the bone screw 10 (e.g., after the bone screw 10 is screwed into place in the bone), the elongate actuator 42 is withdrawn proximally within the elongate channel 38 as illustrated in FIG. 9, thereby allowing the retaining element 40 to be displaced inward to release the undercut feature 24 and thus disengage the bone screw 10.

Figure 10:
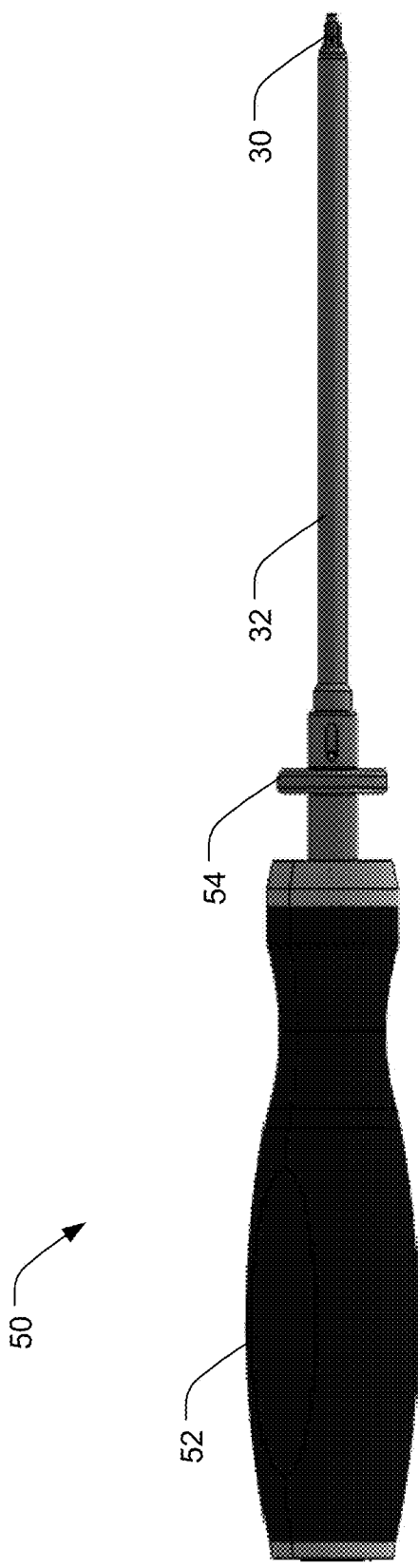
FIG. 10 shows a side view of a retaining driver.

FIG. 10 illustrates one embodiment of a complete retaining driver 50. The retaining driver 50 includes the retaining tip 30 at the distal end of the elongate shaft 32. At the proximal end of the elongate shaft 32, the retaining driver 50 includes a handle 52 sized and shaped to allow a surgeon or other human to hold the retaining driver 50 and to apply rotational torque to it so as to drive in or remove an attached bone screw 10. Additionally, a trigger 54 is provided that is functionally attached to the elongate actuator 42 so that the surgeon or other human holding the retaining driver 50 can engage or release the bone screw 10.

Figure 11:
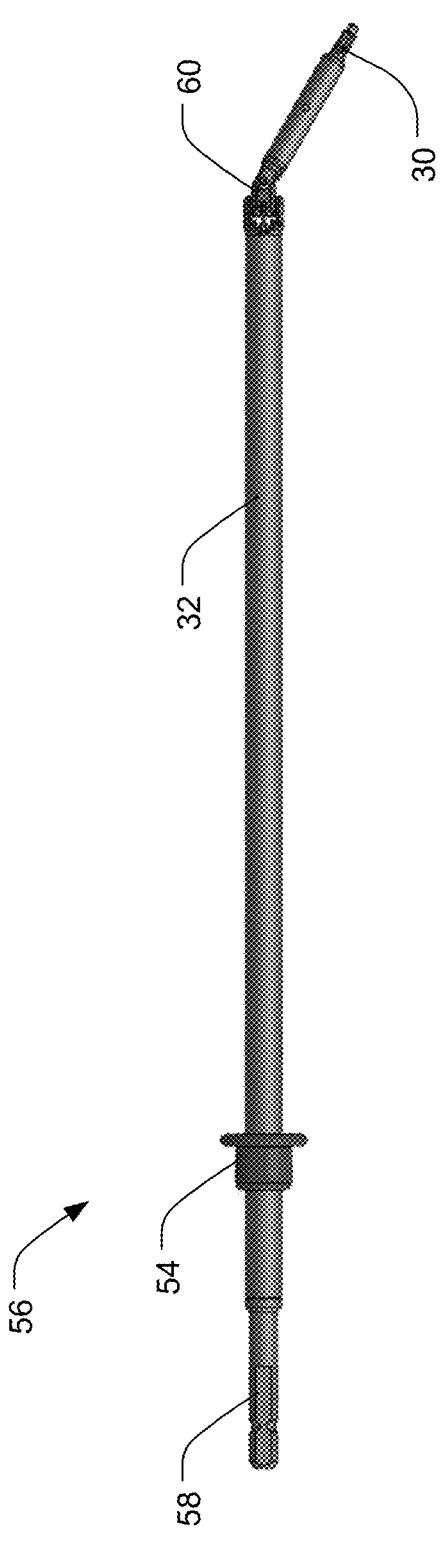
FIG. 11 shows a side view of a retaining driver with an articulating element.
Figure 12:
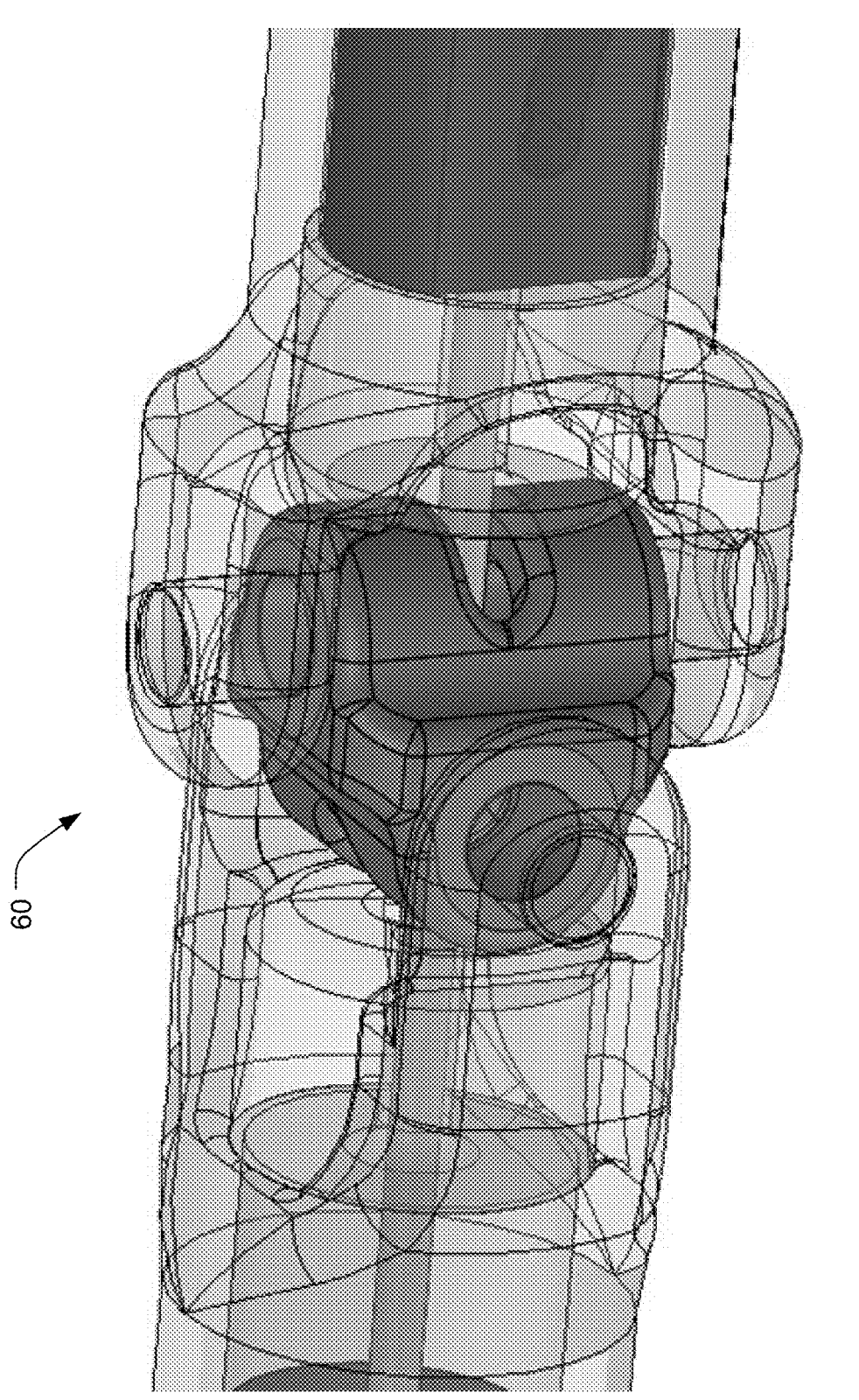
FIG. 12 shows a transparent view of an articulating element.
Figure 13:
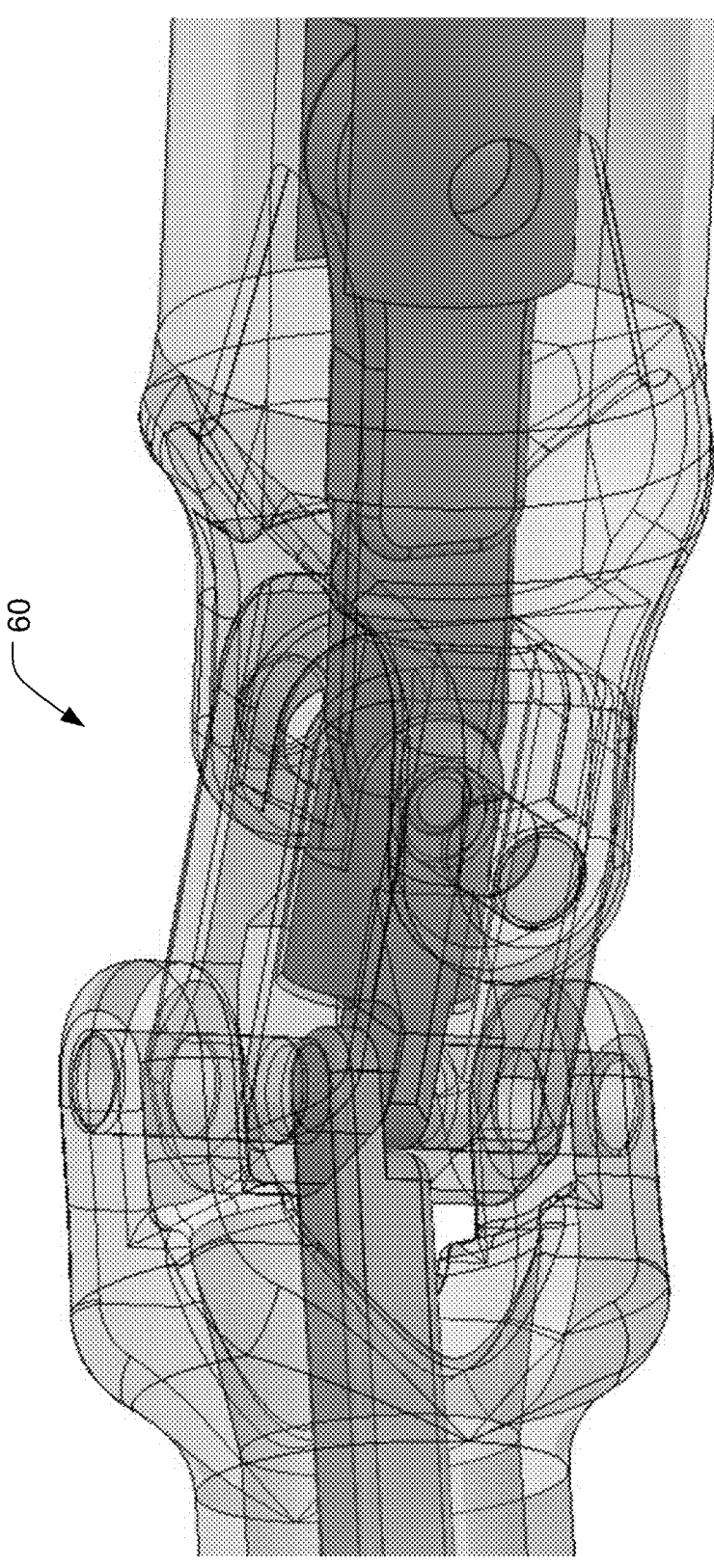
FIG. 13 shows a transparent view of an articulating element.

FIG. 11 illustrates an alternate embodiment of a complete retaining driver 56. This embodiment has similar features to that of FIG. 10, but instead of a handle includes an interface 58 (which may be a quick-connect interface) to permit engagement with a separate handle or handle system. Additionally, this embodiment is articulating and thus includes an articulating element 60, two illustrative embodiments of which are illustrated in FIGS. 12 and 13 in transparent views. In the embodiment of FIG. 12, the elongate actuator 42 passes through the articulating element 60 as a flexible element, such as a nitinol rod, a metal cable, an ultra-high molecular weight polyethylene rod, or a coil spring. In the embodiment of FIG. 13, the elongate actuator passes through the articulating element 60 with its own articulating linkage. In either case, actuating motion of the elongate actuator 42 is passed through the articulating element 60.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A retaining driver for bone screws, the retaining driver comprising:
    a shaft comprising:
        a proximal end of the shaft; and
        a distal end of the shaft;
    an elongate channel extending within the shaft from the distal end of the shaft toward the proximal end of the shaft;
    a retaining tip on the distal end of the shaft, wherein the retaining tip comprises:
        a geometric profile adapted to permit transference of rotational torque to a corresponding geometric profile of a bone screw;
        a window formed on a side of the retaining tip and forming a passage communicating with the elongate channel; and
        a retaining element disposed within the passage and sized to be able to protrude from the window but not to pass entirely through the window;
    an elongate actuator at least partially and movingly disposed within the elongate channel, the elongate actuator comprising a distal shape that is configured to displace the retaining element axially outward in the passage to protrude through the window when the elongate actuator is advanced distally in the elongate channel and which permits the retaining element to move axially inward in the passage when the elongate actuator is displaced proximally within the elongate channel;
    an interface affixed to the proximal end of the shaft to permit affixation of the interface to a handle to facilitate holding of the retaining driver by a practitioner and application of rotational torque thereto;

a trigger functionally secured to a proximal end of the elongate actuator and disposed on the shaft, such that actuation of the trigger causes the elongate actuator to move so as to cause the retaining element to move axially outward or to be released to selectively permit inward axial movement of the retaining element; and
    an articulating joint on the shaft facilitating transference of rotational torque at the proximal end of the shaft to the distal end of the shaft even when the proximal end of the shaft and the distal end of the shaft are not coaxial.

2. The retaining driver as recited in claim 1, wherein the geometric profile of the retaining tip comprises a profile that comprises at least one of a hexalobe profile (Torx™), a hex profile (Allen), a triple-square profile (Robertson), a Torx-Plus™ profile, and a ball-tip version of at least one of the hexalobe profile (Torx™), the hex profile (Allen), the triple-square profile (Robertson), or the Torx-Plus™ profile.

3. The retaining driver as recited in claim 1, wherein the retaining element comprises a form comprising at least one of a sphere, a cylinder with a rounded tip, a pin, a plunger, a rectangular prism with a rounded tip, and a key.

4. The retaining driver as recited in claim 1, wherein distal shape of the elongate actuator comprises a cam profile comprising:
    a dwell at release position at a most distal portion of the retaining driver;
    a primary ramp proximally adjacent the dwell at release position and adapted to provide a first displacement of the retaining element; and
    a secondary ramp proximally adjacent the primary ramp and adapted to provide a second displacement of the retaining element configured to reduce backdriving and to tension the retaining element in the bone screw.

5. The retaining driver as recited in claim 1, wherein distal-proximal movement of the elongate actuator within the shaft is provided by movement comprising at least one of a sliding movement, a rotary movement, and a helical movement.

6. The retaining driver as recited in claim 1, wherein the trigger comprises a ring disposed around the shaft.

7. The retaining driver as recited in claim 6, wherein the articulating joint comprises a first joint configured to articulate along a first axis and a second joint configured to articulate along a second axis.

8. The retaining driver as recited in claim 7, wherein the trigger is disposed proximally of the articulating joint, and wherein the elongate actuator passes through the articulating joint in an articulating form comprising at least one of:
    an articulating actuator joint formed in the elongate actuator; and
    a flexible portion of the elongate actuator comprising at least one of a nitinol wire, a metal cable, an ultra-high molecular weight polyethylene rod, and a coil spring.

9. The retaining driver as recited in claim 1, wherein the retaining element comprises at least one of a plurality of retaining elements that selectively protrudes through a plurality of windows on the retaining tip to selectively retain the bone screw thereon.

10. A retaining driver system comprising:
    a bone screw comprising:
        a threaded shaft comprising:
            a proximal end of the threaded shaft; and
            a distal tip of the threaded shaft;
        a screw head extending proximally from the proximal end of the threaded shaft;

a drive feature extending distally into the screw head from a drive feature opening, the drive feature comprising:

a geometric profile of the bone screw adapted to receive transference of rotational torque when driving the bone screw into bone or when removing the bone screw from bone; and an undercut feature disposed within the drive feature distally from the drive feature opening, such that a diameter of the drive feature distal to the drive feature opening is greater than a diameter of the drive feature opening directly proximate to the undercut feature;

a retaining driver comprising:

a shaft comprising:

a proximal end of the shaft; and a distal end of the shaft;

an elongate channel extending within the shaft from the distal end of the shaft toward the proximal end of the shaft;

a retaining tip on the distal end of the shaft, wherein the retaining tip comprises:

a geometric profile of the retaining tip adapted to permit transference of rotational torque to the geometric profile of the bone screw;

a window formed on a side of the retaining tip so as to be aligned with the undercut feature of the bone screw when the retaining tip is fully inserted into the drive feature of the bone screw, the window forming a passage communicating with the elongate channel; and a retaining element disposed within the passage and sized to be able to protrude from the window but not to pass entirely through the window;

an elongate actuator at least partially and movingly disposed within the elongate channel, the elongate actuator comprising a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel;

an interface affixed to the proximal end of the shaft to permit affixation of the interface to a handle to facilitate holding of the retaining driver by a practitioner and application of rotational torque thereto;

a trigger functionally coupled to a proximal end of the elongate actuator and disposed on the shaft, such that actuation of the trigger causes the elongate actuator to move so as to cause the retaining element to move axially outward or to be released to permit inward axial movement of the retaining element; and an articulating joint on the shaft facilitating transference of rotational torque at the proximal end of the shaft to the distal end of the shaft even when the proximal end of the shaft and the distal end of the shaft are not coaxial.

11. The retaining driver system as recited in claim 10, wherein distal-proximal movement of the elongate actuator within the shaft is provided by movement comprising at least one of sliding movement, rotary movement, and helical movement.

12. The retaining driver system as recited in claim 10, wherein the trigger comprises a ring disposed around the shaft.

13. The retaining driver system as recited in claim 12, wherein the articulating joint comprises a first joint configured to articulate along a first axis and a second joint configured to articulate along a second axis.

14. The retaining driver system as recited in claim 10, wherein the trigger is disposed proximal to the articulating joint and wherein the elongate actuator passes through the articulating joint in an articulating form comprising at least one of:

an articulating actuator joint formed in the elongate actuator; and a flexible portion of the elongate actuator comprising at least one of a nitinol wire, a metal cable, an ultra-high molecular weight polyethylene rod, and a coil spring.

15. The retaining driver system as recited in claim 10, wherein the retaining element comprises at least one of a plurality of retaining elements that selectively protrudes through a plurality of windows on the retaining tip to selectively retain the bone screw thereon.

16. A retaining driver system comprising:

a bone screw comprising:

a threaded shaft comprising:

a proximal end of the threaded shaft; and a distal tip of the threaded shaft;

a screw head extending proximally from the proximal end of the threaded shaft;

a hexalobe drive feature extending distally into the screw head from a drive feature opening, the hexalobe drive feature comprising:

a hexalobe profile of the bone screw adapted to receive transference of rotational torque when driving the bone screw into a bone or when removing the bone screw from the bone; and an undercut feature disposed within the hexalobe drive feature distally from the drive feature opening, such that a diameter of the drive feature distal to the drive feature opening is greater than a diameter of the drive feature opening directly proximate to the undercut feature;

a retaining driver comprising:

a shaft comprising:

a proximal end of the shaft; and a distal end of the shaft;

an elongate channel extending within the shaft from the distal end of the shaft toward the proximal end of the shaft;

a retaining tip on the distal end of the shaft, wherein the retaining tip comprises:

a hexalobe profile of the retaining tip adapted to permit transference of rotational torque to the hexalobe drive feature of the bone screw;

a window disposed on a side of the retaining tip so as to be aligned with the undercut feature of the bone screw when the retaining tip is fully inserted into the drive feature of the bone screw, the window forming a passage communicating with the elongate channel; and a retaining element disposed within the passage and sized to be able to protrude from the window but not to pass entirely through the window;

an elongate actuator at least partially and movingly disposed within the elongate channel, the elongate actuator comprising a distal shape that displaces the retaining element axially outward in the passage to protrude through the window when the elongate actuator is advanced distally in the elongate channel and which permits the retaining element to move axially inward in the passage when the elongate actuator is displaced proximally within the elongate channel; and an articulating joint on the shaft facilitating transference of rotational torque at the proximal end of the shaft to the distal end of the shaft even when the proximal end of the shaft and the distal end of the shaft are not coaxial.

\* \* \* \* \*